US012589174B2

(12) United States Patent
Lim et al.

(10) Patent No.: US 12,589,174 B2
(45) Date of Patent: Mar. 31, 2026

(54) STERILANT STORAGE DEVICE AND STERILIZATION DEVICE

(71) Applicant: PLASMAPP CO., LTD., Daejeon (KR)

(72) Inventors: Youbong Lim, Daejeon (KR); Junyoung Kim, Daejeon (KR); Jeongsan Seo, Daejeon (KR)

(73) Assignee: PLASMAPP CO., LTD., Daejeon (KR)

( * ) Notice: Subject to any disclaimer, the term of this patent is extended or adjusted under 35 U.S.C. 154(b) by 485 days.

(21) Appl. No.: 18/022,880

(22) PCT Filed: Aug. 26, 2021

(86) PCT No.: PCT/KR2021/011485
§ 371 (c)(1),
(2) Date: Feb. 23, 2023

(87) PCT Pub. No.: WO2022/045814
PCT Pub. Date: Mar. 3, 2022

(65) Prior Publication Data
US 2023/0321297 A1     Oct. 12, 2023

(30) Foreign Application Priority Data

Aug. 27, 2020     (KR) ........................ 10-2020-0108217

(51) Int. Cl.
*G01N 21/00*     (2006.01)
*A61L 2/208*     (2026.01)
*B65D 77/04*     (2006.01)
*B65D 81/28*     (2006.01)

(52) U.S. Cl.
CPC .............. *A61L 2/208* (2013.01); *B65D 77/04* (2013.01); *B65D 81/28* (2013.01); *A61L 2202/121* (2013.01); *A61L 2202/15* (2013.01)

(58) Field of Classification Search
CPC .............. A61L 2/186; A61L 2202/181; A61L 2202/182; B01L 3/00
USPC ........................ 422/554, 559, 560, 569, 570
See application file for complete search history.

(56) References Cited

U.S. PATENT DOCUMENTS

2013/0095010 A1*   4/2013   Koyama   ................. A61L 2/186
                                                                     422/554

FOREIGN PATENT DOCUMENTS

JP             03-001871 A       1/1991
JP            2013-090907 A      5/2013
KR       10-2014-0008281 A       1/2014
KR          10-1961945 B1        3/2019
KR       10-2019-0057036 A       5/2019

OTHER PUBLICATIONS

International Search Report of PCT/KR2021/011485 dated Nov. 8, 2021 [PCT/ISA/210].

* cited by examiner

*Primary Examiner* — Monzer R Chorbaji
(74) *Attorney, Agent, or Firm* — Sughrue Mion, PLLC

(57)     ABSTRACT
A sterilant storage device according to an embodiment of the present disclosure includes a first container storing a sterilant therein and including at least a part having air-permeability, and a second container surrounding the first container and formed to be entirely air-impermeable to maintain an internal airtight condition.

16 Claims, 11 Drawing Sheets

STERILANT STORAGE DEVICE AND STERILIZATION DEVICE

CROSS REFERENCE TO RELATED APPLICATIONS

The present application is a U.S. national phase application under 35 U.S.C. 371 of International Application No. PCT/KR2021/011485, filed on Aug. 26, 2021, which claims priority from Korean Patent Application No. 10-2020-0108217 filed on Aug. 27, 2020 in the Korean Intellectual Property Office, the entire disclosure of each of which is incorporated herein by reference.

TECHNICAL FIELD

The present disclosure relates to a sterilant storage device and a sterilization device, and more particularly, to a sterilant storage device and a sterilization device each including a first container storing a sterilant therein and including at least a part having air-permeability, and a second container surrounding the first container and formed to be entirely air-impermeable to maintain an internal airtight condition.

BACKGROUND ART

Most of the sterilizers used in the medical industry use a high-concentration sterilant aqueous solution, and in the sterilization process, the sterilant is vaporized using heat, and then the object to be processed is sterilized by using the vaporized sterilant.

To secure sterility assurance level (SAL) reliability in a sterilization cycle of a sterilizer, an amount and concentration of a sterilant used in the sterilization cycle should be managed to remain constant.

However, due to the thermodynamically unstable state of hydrogen peroxide, etc. used as a sterilant, spontaneous decomposition takes place over time, generating gas in the process.

In other words, there may be the issue of managing the amount and concentration of the sterilant due to chemical decomposition of the sterilant as well as the issue of managing the gas generated by the decomposition of the sterilant.

DISCLOSURE

Technical Goal

The technical goal to be achieved by the present disclosure is to provide a sterilant storage device and a sterilization device each including a first container storing a sterilant therein and including at least a part having air-permeability, and a second container surrounding the first container and formed to be entirely air-impermeable to maintain an internal airtight condition.

Technical Solution

According to an embodiment of the present disclosure, a sterilant storage device includes a first container storing a sterilant therein and including at least a part having air-permeability, and a second container surrounding the first container and formed to be entirely air-impermeable to maintain an internal airtight condition.

According to an embodiment, the first container may store the sterilant therein in a liquid state under an airtight condition.

According to an embodiment, a rate of spontaneous decomposition of the sterilant in the liquid state in the first container may be controlled by an internal pressure of the second container.

According to an embodiment, a part of the first container may be formed of an air-permeable material.

According to an embodiment, the first container may be entirely formed of an air-permeable material.

According to an embodiment, the second container may include a spare space therein excluding an area in which the first container is arranged.

According to an embodiment, the sterilant storage device may further include a sealing member coupled to the first container or the second container and penetrable by a sterilant extractor configured to extract the sterilant.

According to the embodiment, the sealing member may be formed of an elastic material and may restore a path penetrated by the sterilant extractor.

According to an embodiment, the sealing member may extend to another sterilant storage device adjacent to the sterilant storage device.

According to an embodiment, the first container may include a storage portion storing the sterilant and a cover portion covering and sealing an opening of the storage portion.

According to an embodiment, at least a part of the cover portion may be relatively thinner than other parts of the cover portion such that air-permeability is obtained by the at least a part of the cover portion.

According to an embodiment, the second container may include an accommodation portion accommodating at least a part of the cover portion.

According to an embodiment, the accommodation portion may include a spare space into which a spontaneously decomposed sterilant in a gaseous state flows while the cover portion is completely inserted.

According to an embodiment, the sterilant may be hydrogen peroxide.

According to an embodiment of the present disclosure, a sterilization device includes a sterilant storage device storing a sterilant, a sterilant extractor configured to extract the sterilant from the sterilant storage device, and a vaporizer configured to vaporize the extracted sterilant and supply the vaporized sterilant to an area in which an object to be processed is located, wherein the sterilant storage device includes a first container storing the sterilant therein and including at least a part having air-permeability, and a second container surrounding the first container and formed to be entirely air-impermeable to maintain an internal airtight condition.

Advantageous Effects

As a device according to an embodiment of the present disclosure has a double structure including a first container including at least a part having air-permeability and a second container surrounding the first container and formed to be entirely air-impermeable to maintain an internal airtight condition, a rate and amount of spontaneous decomposition of a sterilant may be properly controlled and the gas generated due to the spontaneous decomposition of the sterilant may be managed effectively.

In addition, as the second container of the device according to an embodiment of the present disclosure is formed to be entirely air-impermeable to maintain the internal airtight condition, a sterilant extractor may be easily inserted into the first container.

Moreover, the device according to an embodiment of the present disclosure may prevent leakage of the sterilant to the outside of the sterilant storage device in the process of extracting the sterilant from the sterilant storage device.

DESCRIPTION OF DRAWINGS

Brief description of each drawing is provided to facilitate sufficient understanding of the drawings cited in the detailed description of the present disclosure.

FIG. 1 is a conceptual diagram of a sterilization device according to an embodiment of the present disclosure.

FIG. 7 is a diagram illustrating another embodiment of the sterilant storage unit of FIG. 3.

MODE FOR INVENTION

Figure 2:
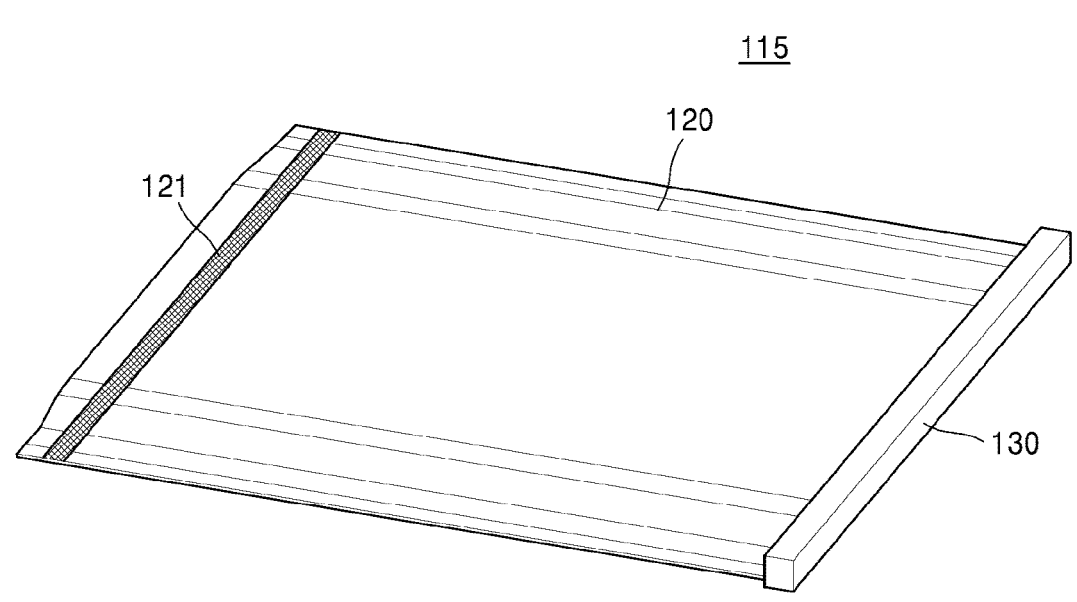
FIG. 2 is a diagram illustrating an embodiment of a pouch of FIG. 1.

As embodiments of the present disclosure allow for various changes and numerous embodiments, exemplary embodiments will be illustrated in the drawings and described in detail in the written description.

However, this is not intended to limit embodiments to particular modes of practice, and it is to be appreciated that all changes, equivalents, and substitutes that do not depart from the spirit and technical scope of the present disclosure are encompassed in embodiments.

In the description of the technical ideas of the present disclosure, certain detailed explanations of the related art are omitted when it is deemed that they may unnecessarily obscure the essence of the present disclosure. While such terms as "first," "second," etc., may be used to describe various components in the present specification, the above terms are used only to distinguish one component from another.

In addition, throughout the present specification, when one component is "coupled to" or "connected to" another component, it should be construed as meaning that one component is directly connected or coupled to another component or one component is coupled or connected indirectly to another component via an intervening component arranged therebetween unless otherwise described.

Terms such as " . . . portion," " . . . device," " . . . member," " . . . module," etc. described in the present specification mean a unit that performs at least one function or operation, and may be implemented by a hardware such as a processor, a micro processor, a micro controller, a central processing unit (CPU), a graphics processing unit (GPU), an accelerate processor unit (APU), a drive signal processor (DSP), an application specific integrated circuit (ASIC), a field programmable gate array (FPGA), etc., a software, or a combination thereof or may be combined with a memory that stores data necessary for processing at least one function or operation.

In the present specification, the components are distinguished from each other based on the primary function of each component. That is, two or more components to be described below may be integrated into one component, or one component may be divided into two or more components by specific functions. In addition, each component to be described below may additionally perform some or all of the functions of other components in addition to its primary function, and some of the primary functions of each component may be fully performed by other components.

Figure 1:
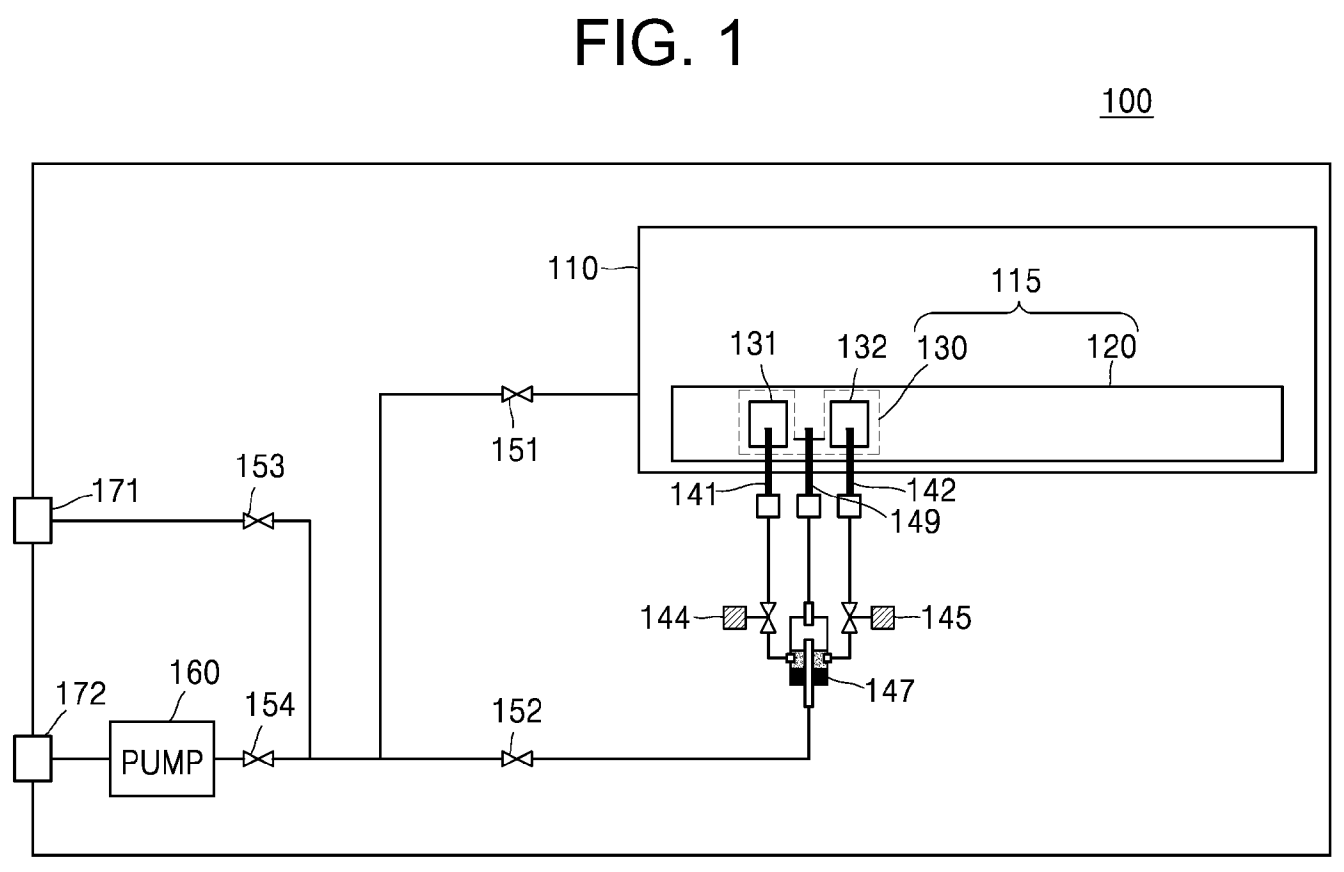
Figure 3:
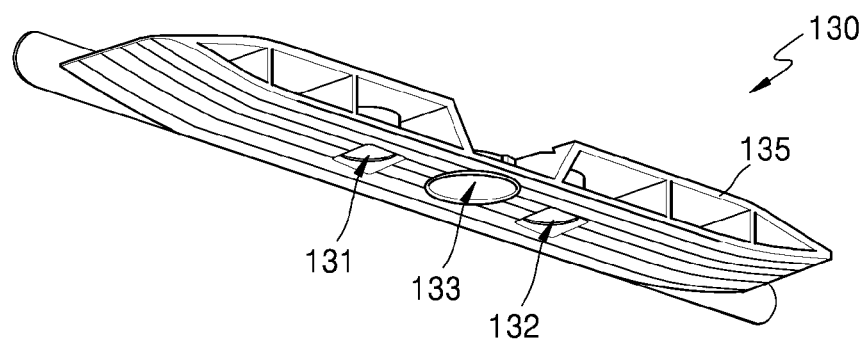
FIG. 3 is a diagram illustrating an embodiment of a sterilant storage device of FIG. 2.

FIG. 1 is a conceptual diagram of a sterilization device according to an embodiment of the present disclosure. FIG. 2 is a diagram illustrating an embodiment of a cartridge of FIG. 1. FIG. 3 is a diagram illustrating an embodiment of a sterilant storage device of FIG. 2.

With reference to FIG. 1, a sterilization device 100 may include a chamber 110, a cartridge 115, sterilant extractors 141 and 142, a plurality of valves 144, 145, and 151 to 154, a vaporizer 147, a sterilant injector 149, a pump 160, and a plurality of filters (171 and 172).

The sterilization device 100 according to an embodiment of the present disclosure may be operated in a chamber mode in which a sterilization target, that is, an object to be processed, is received in the chamber 110 and a sterilization process is performed or in a pouch mode in which the object to be processed is received in a pouch 120 and the sterilization process is performed.

According to an embodiment, the chamber 110 may be a structure which directly accommodates the object to be processed therein, supports the cartridge 115 in which the object to be processed is accommodated, or includes a space for accommodation.

The cartridge 115 may include the pouch 120 and a sterilant storage device 130.

According to an embodiment, the cartridge 115 may be fixed or coupled to one side of the chamber 110.

With reference to FIG. 2, one side of the pouch 120 may be coupled to the sterilant storage device 130, and the other side of the pouch 120 may remain open before the object to be processed is accommodated and may be sealed after the object to be processed is accommodated.

According to an embodiment, the open side of the pouch 120 may be sealed by a method such as thermo-compression bonding, etc., and in this case, a thermo-compression bonding band 121 may be formed.

Returning to FIG. 1, the sterilant storage device 130 may include a plurality of sterilant storage units 131 and 132.

Each of the sterilant storage units 131 and 132 constituting the sterilant storage device 130 may store a sterilant therein.

With reference to FIG. 3, the sterilant storage device 130 may include a frame 135 constituting a frame structure of the sterilant storage device 130, the sterilant storage units 131 and 132 provided in the frame 135, and a sterilant injection passage 133 through which the sterilant injector 149 moves.

The detailed structure of the sterilant storage device 130 will be described later with reference to FIGS. 4 to 7.

Returning to FIG. 1, the sterilant extractors 141 and 142 may penetrate the sterilant storage units 131 and 132 to extract a sterilant stored in each of the sterilant storage units 131 and 132 and deliver the extracted sterilants to the vaporizer 147. According to an embodiment, the sterilization device 100 may further include components for controlling location movements of the sterilant extractors 141 and 142.

The flow of the extracted sterilant may be controlled by a first valve 144 and a second valve 145. The first valve 144 and the second valve 145 may be opened during the sterilant extraction process and closed when the sterilant extraction process is completed.

The vaporizer 147 may vaporize the sterilant extracted by the sterilant extractors 141 and 142, and inject the vaporized sterilant into the pouch 120 of the cartridge 115 through the sterilant injector 149.

Although FIG. 1 describes the case where the sterilant is injected into the pouch 120 of the cartridge 115 according to the pouch mode, the sterilant injector 149 may inject the vaporized sterilant into the chamber 110 when the sterilization device 100 is operated in the chamber mode.

According to an embodiment, in the pouch mode, when the sterilization process performed on the object to be processed in the pouch 120 is completed, an air discharge process for discharging the air in the pouch 120 may be performed, and in this case, a third valve 151 and a fifth valve 153 may be closed, and a fourth valve 152 and a sixth valve 154 may be opened. The air in the pouch 120 may be discharged through the sterilant injector 149.

According to an embodiment, in the chamber mode, when the sterilization process performed on the object to be processed in the chamber 110 is completed, a discharge process for discharging the air in the chamber 110 may be performed, and in this case, the fourth valve 152 and the fifth valve 153 may be closed, and the third valve 151 and the sixth valve 154 may be opened.

According to an embodiment, in the pouch mode, the inside of the pouch 120 may be vented to reach the atmospheric pressure state, and in this case, the third valve 151 and the sixth valve 154 may be closed, and the fourth valve 152 and the fifth valve 153 may be opened. The air in the pouch 120 may be vented through the sterilant injector 149.

According to an embodiment, in the chamber mode, the inside of the chamber 110 may be vented to reach the atmospheric pressure state, and in this case, the fourth valve 152 and the sixth valve 154 may be closed, and the third valve 151 and the fifth valve 153 may be opened.

The pump 160 may apply pressure to discharge the sterilant or the air in the pouch 120 or the chamber 110.

According to an embodiment, the pump 160 may discharge the air inside the chamber 110 or the pouch 120 such that the chamber 110 or the pouch 120 is in a vacuum state before the sterilization process.

According to an embodiment, the pump 160 may discharge the air inside the chamber 110 or the pouch 120 to discharge the remaining sterilant in the chamber 110 or the pouch 120 after the sterilization process.

According to an embodiment, a sterilant decomposition device (not shown) may be further provided at a front end of the pump 160 to decompose the sterilant. For example, the sterilant decomposition device may be a plasma source.

A first filter 171 may filter the air injected into the sterilization device 100 and introduce the filtered air into the sterilization device 100. A second filter 172 may filter the air discharged from the sterilization device 100 and release the filtered air to the outside of the sterilization device 100. According to an embodiment, each of the first filter 171 and the second filter 172 may filter fine dust, germs, etc.

Figure 4:
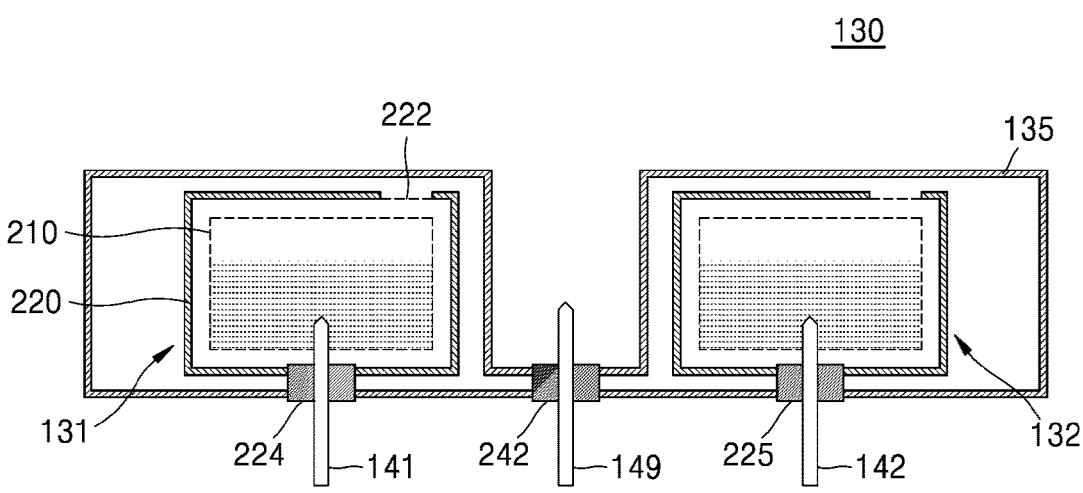
FIG. 4 is a cross-sectional view of a sterilant storage device of FIG. 3 according to an embodiment.

FIG. 4 is a cross-sectional view of a sterilant storage device of FIG. 3 according to an embodiment.

With reference to FIGS. 3 and 4, the sterilant storage device 130 may include the plurality of sterilant storage units 131 and 132 and a plurality of sealing members (224, 225, and 242) in the frame 135.

In FIG. 4, the sterilant extractors 141 and 142 and the sterilant injector 149 are shown along with the sterilant storage device 130, for convenience of description.

A first sterilant storage unit 131 may include a first container 210 and a second container 220.

The first container 210 may store a sterilant therein. According to an embodiment, the first container 210 may store the sterilant therein in a liquid state under an airtight condition.

According to an embodiment, the first container 210 may be entirely formed of an air-permeable material.

In the present specification, the "air-permeable material" may be implemented by polyolefine (PO), such as polyethylene (PE), polypropylene (PP), etc. according to an embodiment, and may be implemented by various materials capable of transmitting gases.

According to an embodiment, the sterilant may be hydrogen peroxide (H2O2) in the liquid state, ethylene oxide (C2H4O), chlorine dioxide (ClO2), etc.

The second container 220 may surround the first container 210, and at least a part 222 of the second container 220 may be formed of an air-permeable material. According to an embodiment, the at least a part 222 of the second container 220 may be located on an upper surface of the second container 220. In the second container 220, the position and size of the at least a part 222 formed of an air-permeable material may be changed in various ways.

According to an embodiment, the other parts of the second container 220 excluding the at least a part 222 of the second container 220 may be formed of an air-impermeable material.

In the present specification, the term "air-impermeable material" includes a material through which gases cannot be physically transmitted.

In the present specification, the "air-impermeable material" may be implemented by polyamide-based resin such as nylon, etc., styrene-based resin such as acrylonitrile butadiene styrene (ABS) resin, an inorganic film such as an aluminum film, etc., according to an embodiment.

According to an embodiment, the other parts of the second container 220 excluding the at least a part 222 of the second container 220 may include a material having a relatively high chemical resistance to a sterilant, compared to a material of the at least a part 222 of the second container 220.

According to an embodiment, the air-permeability of the air-permeable material forming the at least a part 222 of the second container may be relatively higher than the air-permeability of the air-permeable material forming the first container 210. In this case, the air-permeable material forming the first container 210 may have a certain quality and thickness that allow proper control of the spontaneous decomposition rate of the sterilant stored inside the first container 210. For example, the air-permeable material forming the first container 210 may be implemented such that an amount of loss of the sterilant in the first container 210 during the shelf life of a product is less than 5%. In addition, as the air-permeability of the air-permeable material forming the at least a part 222 of the second container is higher than the air-permeability of the air-permeable material forming the first container 210, the gas released out of the first container 210 may be effectively discharged.

A first sealing member 224 may be coupled to at least one of the first container 210 and the second container 220, and may be penetrated by a sterilant extractor 141.

According to an embodiment, the first sealing member 224 may be formed of an elastic material and may restore the path penetrated by the sterilant extractor 141.

When the sterilant extractor 141 penetrates the first sealing member 224 and the first container 210 to extract the sterilant inside the first container 210, and some of the sterilant leak from the sterilant extractor 141, external leakage of the sterilant may be prevented by the second container 220.

A second sterilant storage unit 132 may be substantially the same as the first sterilant storage unit 131, and a second sealing member 225 may be substantially the same as the first sealing member.

A third sealing member 242 may be coupled to the frame 135 of the sterilant storage device 130, and may maintain the sealed state such that the sterilant injected into the pouch 120 from the sterilant injector 149 does not leak outside the sterilant storage device.

According to an embodiment, the third sealing member 242 may be formed of an elastic material and may restore the path penetrated by the sterilant injector 149.

Figure 5:
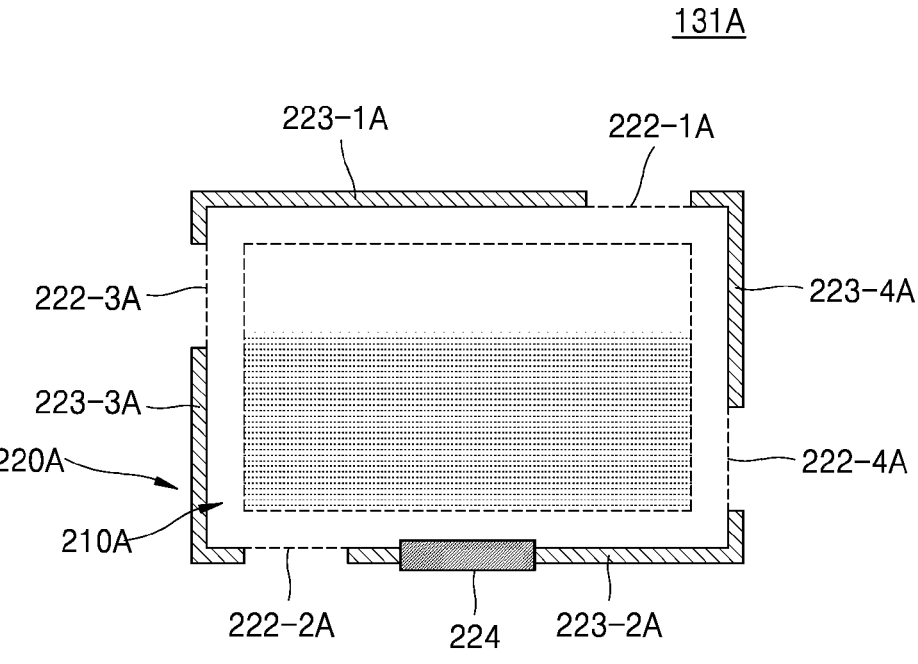
FIG. 5 is a diagram illustrating another embodiment of a sterilant storage unit of FIG. 3.

FIG. 5 is a diagram illustrating another embodiment of a sterilant storage unit of FIG. 3.

With reference to FIGS. 3 to 5, according to another embodiment of a sterilant storage unit 131A, a first container 210A may be entirely formed of an air-permeable material.

First areas 222-1A to 222-4A of a second container 220A may be formed of an air-permeable material, and second areas 223-1A to 223-4A of the second container 220A may be formed of an air-impermeable material.

According to an embodiment, the first areas 222-1A to 222-4A of the second container 220A which are formed of an air-permeable material may be located on a plurality of surfaces of the second container 220A.

According to an embodiment, the first areas 222-1A to 222-4A of the second container 220A which are formed of an air-permeable material may be formed only on two surfaces of the second container 220A that face each other (for example, an upper surface and a lower surface, lateral surfaces facing each other, etc.)

Figure 6:
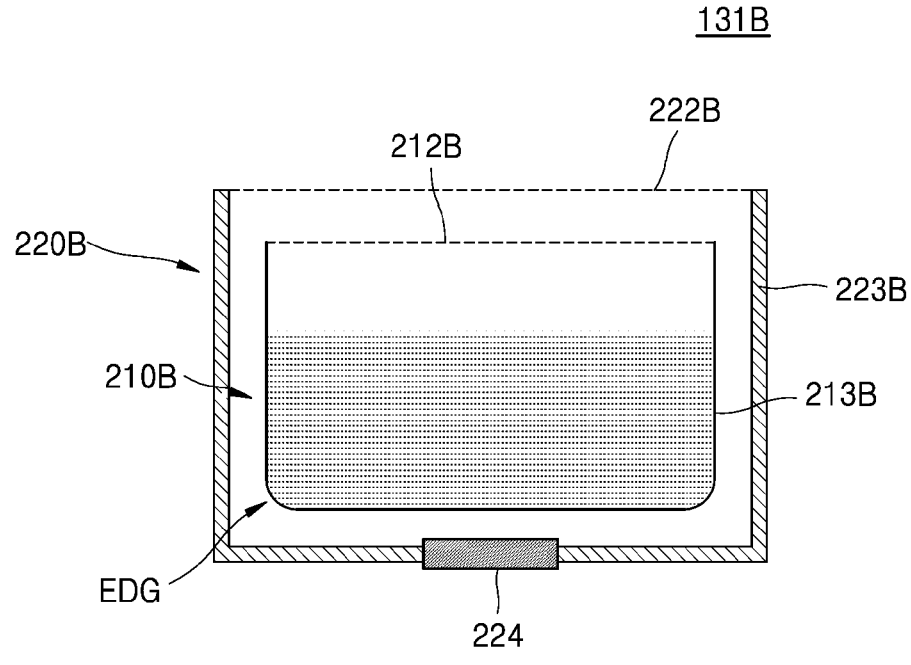
FIG. 6 is a diagram illustrating another embodiment of the sterilant storage unit of FIG. 3.

FIG. 6 is a diagram illustrating another embodiment of the sterilant storage unit of FIG. 3.

With reference to FIGS. 3 to 6, according to another embodiment of a sterilant storage unit 131B, a first area 212B of a first container 210B may be formed of an air-permeable material, and a second area 213B of the first container 210B may be formed of an air-impermeable material.

According to an embodiment, the first area 212B of the first container 210B, which is formed of an air-permeable material may have a structure covering an opening formed by the second area 213B of the first container 210B such that the sterilant in the liquid state is stored inside the first container 210B under an airtight condition.

According to an embodiment, the first area 212B of the first container 210B may be implemented in a form of a film.

According to an embodiment, the material of the second area 213B of the first container 210B may have a relatively high chemical resistance to the sterilant, compared to the material of the first area 212B.

According to an embodiment, the first container 210B may have a shape including a symmetrical structure of both sides of at least one cross-section. For example, in the cross-section of FIG. 6, the shape of the first container 210B may have a bilateral symmetrical structure.

According to an embodiment, assuming that the cross-section in FIG. 6 is an X-Z axis cross-section, the shape of the first container 210B may have a structure in which both the X-Z axis cross-section and the X-Y axis cross-section are symmetrical.

According to an embodiment, at least some of edges EDG of the first container 210B may be formed as a curved surface.

Figure 7:
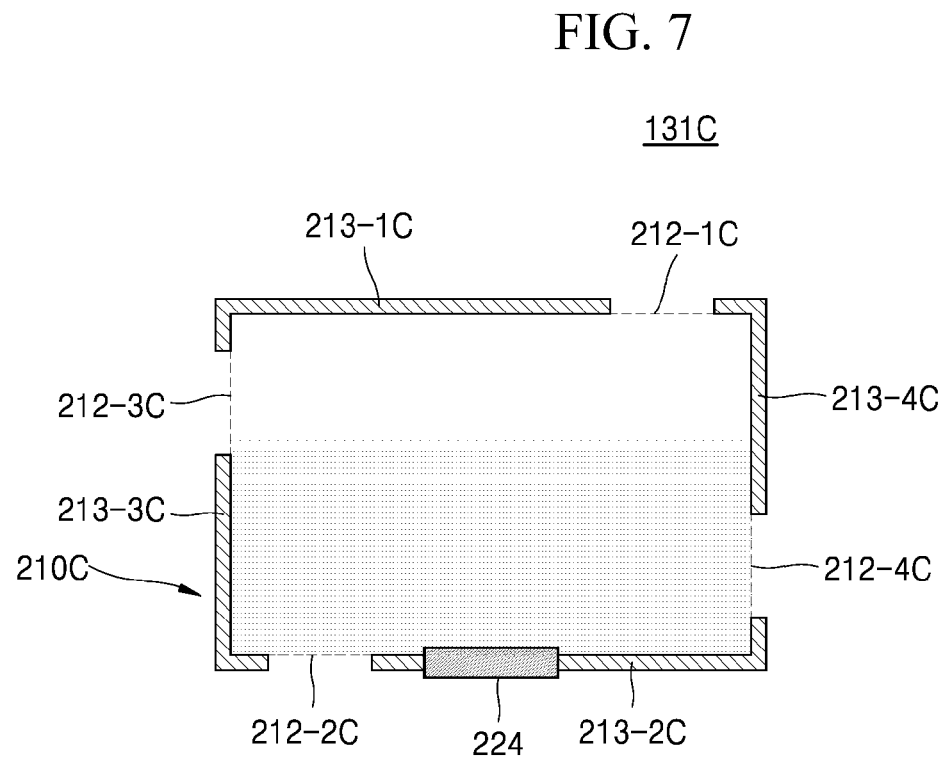

FIG. 7 is a diagram illustrating another embodiment of the sterilant storage unit of FIG. 3.

With reference to FIGS. 3 to 7, another embodiment of a sterilant storage unit 131C may only include a first container 210C without a second container.

First areas 212-1C to 212-4C of the first container 210C may be formed of an air-permeable material, and second areas 213-1C to 213-4C may be formed of an air-impermeable material.

According to an embodiment, the positions and sizes of the first areas 212-1C to 212-4C formed of an air-permeable material may be modified in various ways.

According to an embodiment, the first areas 212-1C to 212-4C of the first container 210C which are formed of an air-permeable material may be formed only on two surfaces of the first container 210C that face each other (for example, an upper surface and a lower surface, lateral surfaces facing each other, etc.)

According to an embodiment, the first container 210C may have a structure that is symmetrical in all directions (e.g., a cube shape, a sphere shape, etc.)

Figure 8:
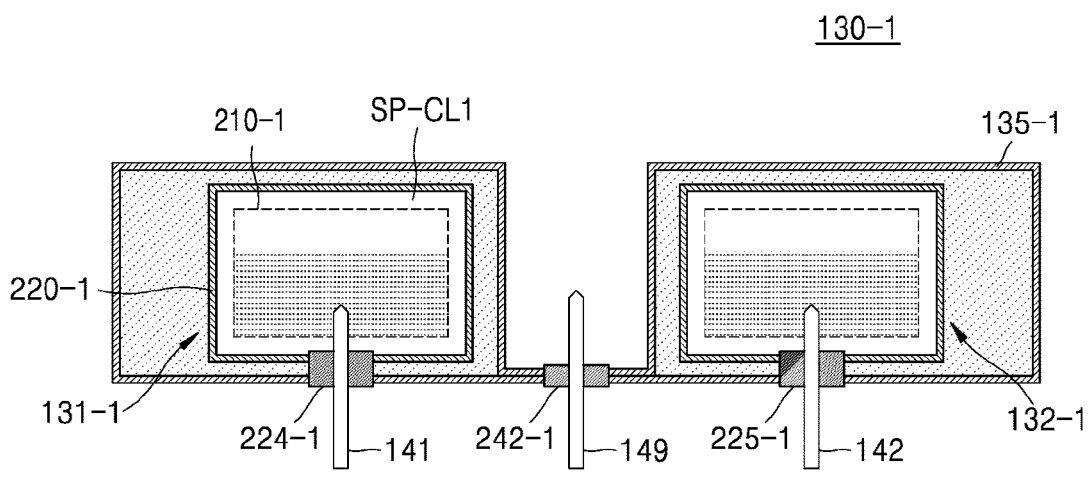
FIG. 8 is a cross-sectional view of a sterilant storage device of FIG. 3 according to another embodiment.

FIG. 8 is a cross-sectional view of a sterilant storage device of FIG. 3 according to another embodiment.

With reference to FIGS. 3 and 8, the sterilant storage device 130-1 may include a plurality of sterilant storage units 131-1 and 132-1 and a plurality of sealing members 224-1, 225-1, and 242-1 in a frame 135-1.

In FIG. 8, the sterilant extractors 141 and 142 and the sterilant injector 149 are shown along with the sterilant storage device 130-1, for convenience of description.

A first sterilant storage unit 131-1 may include a first container 210-1 and a second container 220-1.

The first container 210-1 may store a sterilant therein. According to an embodiment, the first container 210-1 may store the sterilant therein in the liquid state under an airtight condition.

According to an embodiment, at least a part of the first container 210-1 may have air-permeability. For example, the material constituting the first container 210-1 itself may be an air-permeable material or the first container 210-1 may be structurally air-permeable while the material forming the first container 210-1 is an air-impermeable material.

According to an embodiment, when the material of the first container 210-1 is an air-permeable material, the first container 210-1 may be partially or entirely formed of an air-permeable material.

In the present specification, the "air-permeable material" may be implemented by polyolefine (PO), such as polyethylene (PE), polypropylene (PP), etc. according to an embodiment, and may be implemented by various materials capable of transmitting gases.

According to an embodiment, the sterilant may be hydrogen peroxide ($H_2O_2$) in the liquid state, ethylene oxide ($C_2H_4O$), chlorine dioxide ($ClO_2$), etc.

The second container 220-1 may surround the first container 210-1 and may be entirely air-impermeable to maintain the internal airtight condition.

According to an embodiment, the second container 220-1 may be entirely formed of an air-impermeable material or may be structurally air-impermeable.

In the present specification, the "air-impermeable material" may be implemented by polyamide-based resin such as nylon, etc., styrene-based resin such as acrylonitrile butadiene styrene (ABS) resin, an inorganic film such as aluminum film, etc., according to an embodiment.

According to an embodiment, the first container 210-1 and the second container 220-1 may be formed of a material having high chemical resistance to the sterilant.

The sterilant in the liquid state stored inside the first container 210-1 may by changed into a gaseous state due to the spontaneous decomposition. The sterilant in the gaseous state may pass through the first container 210-1 partially having air-permeability and move to an area outside the first container 210-1 and inside the second container 220-1 to reach a state of equilibrium.

In the state of equilibrium, the spontaneous decomposition of the sterilant may be controlled. At this time, the rate of spontaneous decomposition of the sterilant in the liquid state or the amount of loss due to the spontaneous decomposition of the sterilant in the first container 210-1 may be controlled by the pressure inside the second container 220-1.

The second container 220-1 may include a spare space SP-CL1 excluding an area in which the first container 210-1 is arranged. The sterilant in the gaseous state discharged according to the spontaneous decomposition of the sterilant in the first container 210-1 may flow into the spare space SP-CL1.

A first sealing member 224-1 may be coupled to at least one of the first container 210-1 and the second container 220-1, and may be penetrated by a sterilant extractor 141.

According to an embodiment, the first sealing member 224-1 may be formed of an elastic material and may restore the path penetrated by the sterilant extractor 141.

When the sterilant extractor 141 penetrates the first sealing member 224-1 and the first container 210-1 to extract the sterilant inside the first container 210-1, and some of the sterilant leak from the sterilant extractor 141, external leakage of the sterilant may be prevented by the second container 220-1.

A second sterilant storage unit 132-1 may be substantially the same as the first sterilant storage unit 131-1, and a second sealing member 225-1 may be substantially the same as the first sealing member 224-1.

A third sealing member 242-1 may be coupled to the frame 135-1 of the sterilant storage device 130-1, and may maintain the sealed state such that the sterilant injected into the pouch 120 from the sterilant injector 149 does not leak outside the sterilant storage device.

According to an embodiment, the third sealing member 242-1 may be formed of an elastic material and may restore the path penetrated by the sterilant injector 149.

According to an embodiment, each of the first sealing member 224-1, the second sealing member 225-1, and the third sealing member 242-1 may be formed of an elastic material. Each of the first sealing member 224-1, the second sealing member 225-1, and the third sealing member 242-1 may restore the penetrated path when the sterilant extractors 141 and 142 or the sterilant injector 149 is out of the path after the penetration.

According to an embodiment, the first sealing member 224-1 may extend to another sterilant storage unit 132-1 adjacent to the first sterilant storage unit 131-1. In this case, the first sealing member 224-1, the second sealing member

225-1, and the third sealing member 242-1 may be connected to each other to form a single member.

Figure 9:
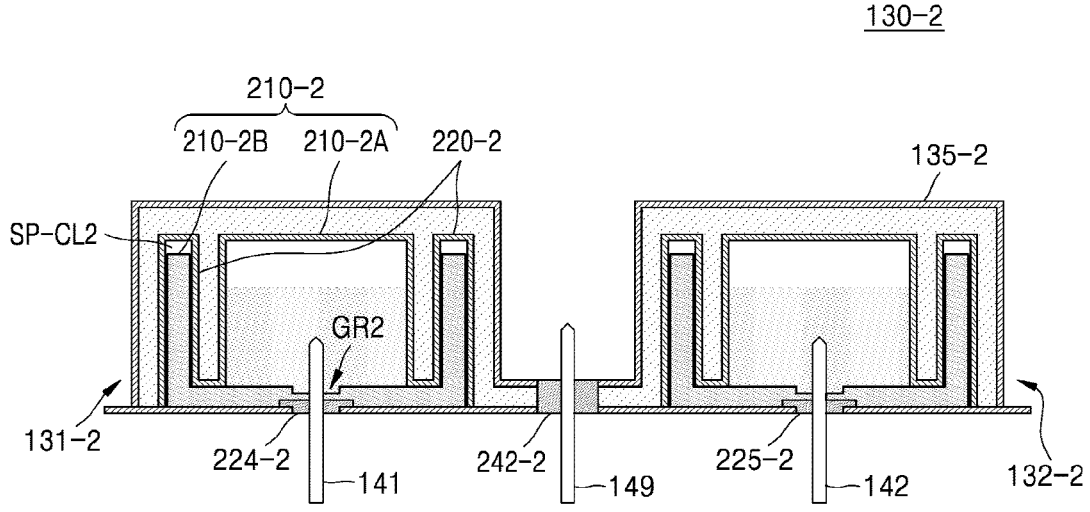
FIG. 9 is a cross-sectional view of the sterilant storage device of FIG. 3 according to another embodiment.
Figure 10:
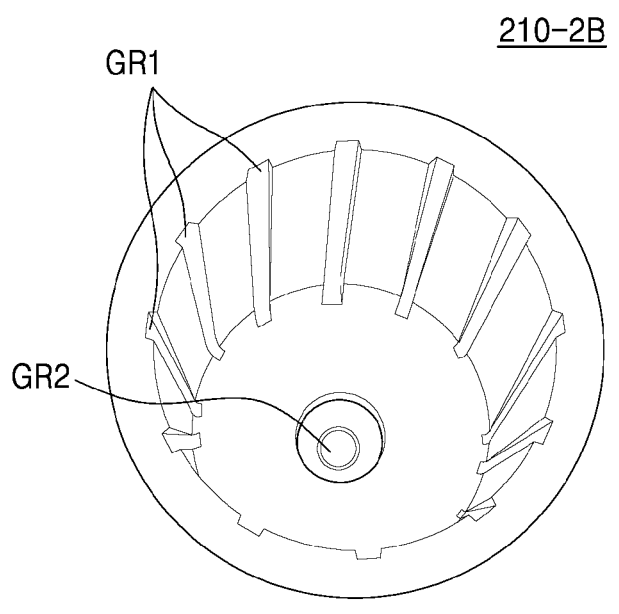
FIG. 10 is a diagram illustrating an embodiment of a cover portion of FIG. 9.

FIG. 9 is a cross-sectional view of the sterilant storage device of FIG. 3 according to another embodiment. FIG. 10 is a diagram illustrating an embodiment of a cover portion of FIG. 9.

With reference to FIGS. 3, 9, and 10, a sterilant storage device 130-2 may include a plurality of sterilant storage units (131-2 and 132-2) and a plurality of sealing members (224-2, 225-2, and 242-2) in a frame 135-2.

In FIG. 9, the sterilant extractors 141 and 142 and the sterilant injector 149 are shown along with the sterilant storage device 130-2, for convenience of description.

A first sterilant storage unit 131-2 may include a first container 210-2 and a second container 220-2.

The first container 210-2 may include a storage portion 210-2A and a cover portion 210-2B.

The storage portion 210-2A may contain and store a sterilant therein. An opening may be formed on one side of the storage portion 210-2A.

According to an embodiment, the storage portion 210-2A may be a partial space formed according to the internal structure of the frame 135-2.

The cover portion 210-2B may cover the opening of the storage portion 210-2A to seal the inside of the storage portion 210-2A.

At least a part of the cover portion 210-2B may be relatively thinner than the other parts, and thus, the cover portion 210-2B may have air-permeability due to the part having a relatively thin thickness.

With reference to FIG. 10, a plurality of first grooves GR1 and a plurality of second grooves GR2 may be formed in the cover portion 210-2B.

The plurality of first grooves GR1 may form a path when the cover portion 210-2B and the storage portion 210-2A are engaged with each other to mitigate the pressure applied to the spare space when the sterilant spontaneously decomposed or vaporized flows in a direction of a sidewall which is relatively thin.

The area of the cover portion 210-2B in which the second grooves GR2 may be relatively thinner than the rest of the cover portion 210-2B to have air-permeability.

According to an embodiment, the cover portion 210-2B may be formed of an air-permeable material, and the degree of air-permeability may vary depending on its thickness.

Returning to FIG. 9, the second container 220-2 may include an accommodation space surrounding and accommodating at least a part of the cover portion 210-2B.

The accommodation space of the second container 220-2 may include a spare space SP-CL2 into which the spontaneously decomposed sterilant may flow while the cover portion 210-2B is completely inserted.

According to an embodiment, the second container 220-2 may be a partial space formed according to the internal structure of the frame 135-2.

The structure and operation of the plurality of sealing members (224-2, 225-2, and 242-2) and the sterilant extractors 141 and 142 and the sterilant injector 149 which are capable of penetrating the plurality of sealing members (224-2, 225-2, and 242-2) may be substantially the same as the structure and operation of the plurality of sealing members (224, 225, and 242) and the sterilant extractors 141 and 142 and the sterilant injector 149 which are capable of penetrating the plurality of sealing members (224, 225, and 242) shown in FIG. 4.

A second sterilant storage unit 132-2 may have substantially the same structure as the first sterilant storage unit 131-2.

Figure 11:
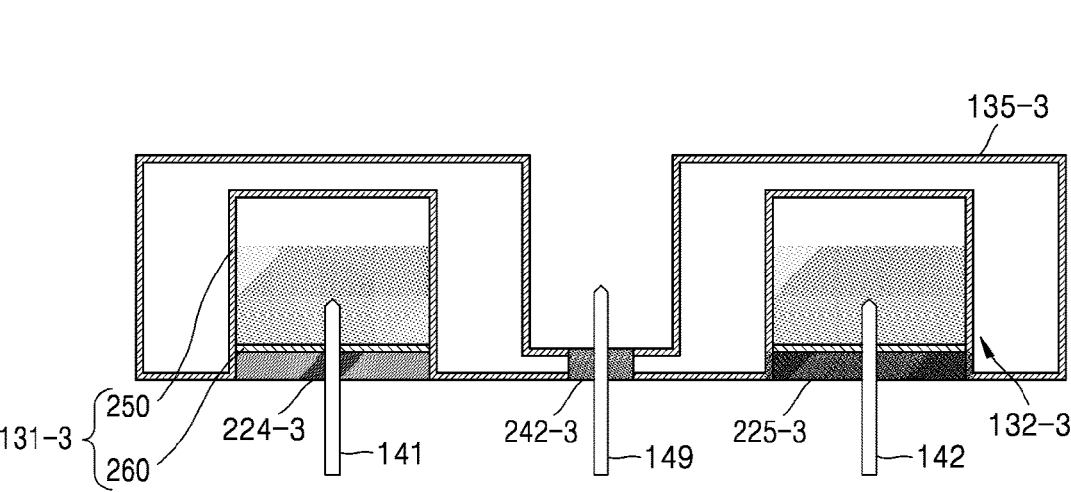
FIG. 11 is a cross-sectional view of the sterilant storage device of FIG. 3 according to another embodiment.

FIG. 11 is a cross-sectional view of the sterilant storage device of FIG. 3 according to another embodiment.

With reference to FIGS. 3 and 11, a sterilant storage device 130-3 may include a plurality of sterilant storage units (131-3 and 132-3) and a plurality of sealing members (224-3, 225-3, and 242-3) in a frame 135-3.

In FIG. 11, the sterilant extractors 141 and 142 and the sterilant injector 149 are shown along with the sterilant storage device 130-3, for convenience of description.

A first sterilant storage unit 131-3 may include a storage portion 250 and a cover portion 260.

The storage portion 250 may contain and store a sterilant therein. An opening may be formed on one side of the storage portion 250.

According to an embodiment, the storage portion 250 may be a partial space formed according to the internal structure of the frame 135-3.

The cover portion 260 may cover the opening of the storage portion 250 to seal the inside of the storage portion 250.

According to an embodiment, the cover portion 260 may be formed of an air-impermeable material.

According to another embodiment, the cover portion 260 may be partially or entirely formed of an air-permeable material. When the cover portion 260 is partially or entirely formed of an air-permeable material, the inside of the storage portion 250 may be sealed by a sealing member 224-3.

The structure and operation of the plurality of sealing members (224-3, 225-3, and 242-3) and the sterilant extractors 141 and 142 and the sterilant injector 149 which are capable of penetrating the plurality of sealing members (224-3, 225-3, and 242-3) may be substantially the same as the structure and operation of the plurality of sealing members (224, 225, and 242) and the sterilant extractors 141 and 142 and the sterilant injector 149 which are capable of penetrating the plurality of sealing members (224, 225, and 242) shown in FIG. 4.

A second sterilant storage unit 132-3 may have substantially the same structure as the first sterilant storage unit 131-3.

According to an embodiment, in the structure of the sterilant storage units (131, 131A to 131C, 131-1 to 131-3, 132, and 132-1 to 132-3) shown in FIGS. 4 to 11, the structures of the first container and the second container may be provided at least partially in combination with each other.

In the present specification, the sterilant storage units (131, 131A to 131C, 131-1 to 131-3, 132, and 132-1 to 132-3) may also be referred to as a sterilant storage device.

Although the present disclosure describes in detail preferred embodiments, the present disclosure is not limited thereto, and the embodiments may be modified and changed in various ways by a person of ordinary skill in the pertinent art within the technical ideas and scope of the present disclosure.

The invention claimed is:

1. A sterilant storage device comprising:
a first container storing a sterilant therein and including at least a part having air-permeability; and
a second container surrounding the first container and being formed of an air-permeable material in part and an air-impermeable material in a remaining part.

2. The sterilant storage device of claim 1, wherein the first container stores the sterilant therein in a liquid state under an airtight condition.

3. The sterilant storage device of claim 2, wherein a rate of spontaneous decomposition of the sterilant in the liquid state in the first container is controlled by an internal pressure of the second container.

4. The sterilant storage device of claim 1, wherein a part of the first container is formed of an air-permeable material.

5. The sterilant storage device of claim 1, wherein the first container is entirely formed of an air-permeable material.

6. The sterilant storage device of claim 1, wherein the second container includes a spare space therein excluding an area in which the first container is arranged.

7. The sterilant storage device of claim 1, further comprising a sealing member coupled to the first container or the second container and penetrable by a sterilant extractor configured to extract the sterilant.

8. The sterilant storage device of claim 7, wherein the sealing member is formed of an elastic material and is capable of restoring a path penetrated by the sterilant extractor.

9. The sterilant storage device of claim 8, wherein the sealing member extends to another sterilant storage device adjacent to the sterilant storage device.

10. The sterilant storage device of claim 1, wherein the first container includes:
a storage portion storing the sterilant; and
a cover portion covering and sealing an opening of the storage portion.

11. The sterilant storage device of claim 10, wherein at least a part of the cover portion is relatively thinner than other parts of the cover portion such that air-permeability is obtained by the at least a part of the cover portion.

12. The sterilant storage device of claim 10, wherein the second container includes an accommodation space accommodating at least a part of the cover portion.

13. The sterilant storage device of claim 12, wherein the accommodation space includes a spare space into which a spontaneously decomposed sterilant in a gaseous state flows while the cover portion is completely inserted.

14. The sterilant storage device of claim 1, wherein the sterilant is hydrogen peroxide.

15. The sterilant storage device of claim 1, wherein the air-permeable material forming at least a part of the second container has a higher air-permeability than an air-permeable material forming at least a part of the first container.

16. A sterilization device comprising:
a sterilant storage device storing a sterilant;
a sterilant extractor configured to extract the sterilant from the sterilant storage device; and
a vaporizer configured to vaporize the extracted sterilant and supply the vaporized sterilant to an area in which an object to be processed is located,
wherein the sterilant storage device includes:
a first container storing the sterilant therein and including at least a part having air-permeability; and
a second container surrounding the first container and being formed of an air-permeable material in part and an air-impermeable material in a remaining part.

* * * * *